(12) United States Patent
Gilbert et al.

(10) Patent No.: US 9,752,976 B2
(45) Date of Patent: Sep. 5, 2017

(54) OPTICAL DETECTOR FOR A PARTICLE SORTING SYSTEM

(71) Applicant: CYTONOME/ST, LLC, Boston, MA (US)

(72) Inventors: John R. Gilbert, Brookline, MA (US); Edward Sinofsky, Dennis, MA (US); Manish Deshpande, Canton, MA (US)

(73) Assignee: CYTONOME/ST, LLC, Boston, MA (US)

(*) Notice: Subject to any disclaimer, the term of this patent is extended or adjusted under 35 U.S.C. 154(b) by 0 days.

(21) Appl. No.: 14/629,057

(22) Filed: Feb. 23, 2015

(65) Prior Publication Data

US 2015/0233813 A1    Aug. 20, 2015

Related U.S. Application Data

(60) Continuation of application No. 12/966,654, filed on Dec. 13, 2010, now Pat. No. 8,964,184, which is a
(Continued)

(51) Int. Cl.
*G01N 21/00* (2006.01)
*G01N 15/14* (2006.01)
*G01N 15/10* (2006.01)

(52) U.S. Cl.
CPC ..... *G01N 15/1434* (2013.01); *G01N 15/1459* (2013.01); *G01N 15/1484* (2013.01); *G01N 2015/1081* (2013.01)

(58) Field of Classification Search
CPC ........... G01N 15/1404; G01N 15/1434; G01N 15/1459; G01N 15/1484
(Continued)

(56) References Cited

U.S. PATENT DOCUMENTS

| 4,004,150 A | 1/1977 | Natelson |
| 4,498,353 A | 2/1985 | Kitade |

(Continued)

FOREIGN PATENT DOCUMENTS

| EP | 0644417 A1 | 3/1995 |
| EP | 0793098 A1 | 9/1997 |

(Continued)

OTHER PUBLICATIONS

Communication pursuant to Article 94(3) EPC issued in European Application No. 04786510.0-1524, dated Jun. 10, 2011.
(Continued)

*Primary Examiner* — Hoa Pham
(74) *Attorney, Agent, or Firm* — McCarter & English, LLP; David R. Burns

(57) ABSTRACT

An optical system for acquiring fast spectra from spatially channel arrays includes a light source for producing a light beam that passes through the microfluidic chip or the channel to be monitored, one or more lenses or optical fibers for capturing the light from the light source after interaction with the particles or chemicals in the microfluidic channels, and one or more detectors. The detectors, which may include light amplifying elements, detect each light signal and transducer the light signal into an electronic signal. The electronic signals, each representing the intensity of an optical signal, pass from each detector to an electronic data acquisition system for analysis. The light amplifying element or elements may comprise an array of phototubes, a multianode phototube, or a multichannel plate based image intensifier coupled to an array of photodiode detectors.

19 Claims, 8 Drawing Sheets

Related U.S. Application Data continuation of application No. 12/370,237, filed on Feb. 12, 2009, now abandoned, which is a continuation of application No. 11/906,621, filed on Oct. 3, 2007, now Pat. No. 7,492,522, which is a division of application No. 10/915,016, filed on Aug. 9, 2004, now Pat. No. 7,298,478.

(60) Provisional application No. 60/495,374, filed on Aug. 14, 2003.

(58) Field of Classification Search
USPC .................................. 356/246, 73, 335–343
See application file for complete search history.

(56) References Cited

U.S. PATENT DOCUMENTS

| | | | |
|---|---|---|---|
| 4,498,780 A | | 2/1985 | Banno et al. |
| 4,498,782 A | | 2/1985 | Proctor et al. |
| 4,560,865 A | | 12/1985 | Bergstrom |
| 4,717,655 A | * | 1/1988 | Fulwyler ............... C12Q 1/04 435/34 |
| 4,797,696 A | | 1/1989 | Allen et al. |
| 4,983,359 A | * | 1/1991 | Tomioka ............ G01N 15/1459 356/39 |
| 4,987,432 A | | 1/1991 | Landwehr |
| 5,216,488 A | | 6/1993 | Tguunanen et al. |
| 5,307,144 A | | 4/1994 | Hiroshi et al. |
| 5,644,388 A | | 7/1997 | Maekawa et al. |
| 5,867,266 A | | 2/1999 | Craighead |
| 6,197,575 B1 | | 3/2001 | Griffith et al. |
| 6,221,226 B1 | | 4/2001 | Kopf-Sill |
| 6,316,781 B1 | | 11/2001 | Nagle et al. |
| 6,337,740 B1 | | 1/2002 | Parce |
| 6,353,475 B1 | | 3/2002 | Jensen et al. |
| 6,361,672 B1 | | 3/2002 | Zhu et al. |
| 6,381,073 B1 | | 4/2002 | Wilson |
| 6,445,448 B1 | * | 9/2002 | Melman ........... G01N 27/44721 356/246 |
| 6,496,260 B1 | | 12/2002 | Hafeman et al. |
| 6,504,607 B2 | | 1/2003 | Jensen et al. |
| 6,534,011 B1 | | 3/2003 | Karthe et al. |
| 6,567,163 B1 | | 5/2003 | Sandstrom |
| 6,580,507 B2 | | 6/2003 | Fry et al. |
| 6,602,702 B1 | | 8/2003 | McDevitt et al. |
| 6,616,823 B2 | | 9/2003 | Kopf-Sill |
| 6,632,400 B1 | | 10/2003 | Brennen et al. |
| 6,649,403 B1 | | 11/2003 | McDevitt et al. |
| 6,674,525 B2 | | 1/2004 | Bardell et al. |
| 6,674,572 B1 | * | 1/2004 | Scheruebl .......... G02B 21/0024 356/237.5 |
| 6,703,205 B2 | | 3/2004 | Kopf-Sill et al. |
| 6,744,038 B2 | | 6/2004 | Wang et al. |
| 6,747,285 B2 | | 6/2004 | Schueller et al. |
| 6,756,019 B1 | | 6/2004 | Dubrow et al. |
| 6,759,662 B1 | | 7/2004 | Li |
| 6,767,706 B2 | | 7/2004 | Quake et al. |
| 6,771,421 B2 | | 8/2004 | Rope et al. |
| 6,930,314 B2 | | 8/2005 | Jackson, III et al. |
| 6,980,303 B2 | | 12/2005 | Kume et al. |
| 7,298,478 B2 | | 11/2007 | Gilbert et al. |
| 7,355,699 B2 | | 4/2008 | Gilbert et al. |
| 7,492,522 B2 | | 2/2009 | Gilbert et al. |
| 7,576,861 B2 | | 8/2009 | Gilbert et al. |
| 2002/0071121 A1 | | 6/2002 | Ortyn et al. |
| 2004/0017570 A1 | | 1/2004 | Parikh et al. |
| 2006/0073599 A1 | | 4/2006 | Weigl et al. |
| 2007/0076199 A1 | | 4/2007 | Ode |
| 2008/0030865 A1 | | 2/2008 | Gilbert et al. |
| 2008/0180666 A1 | | 7/2008 | Gilbert et al. |
| 2009/0168053 A1 | | 7/2009 | Gilbert et al. |
| 2009/0317806 A1 | | 12/2009 | Hasson |
| 2015/0329617 A1 | * | 11/2015 | Winther ........... C07K 14/70539 436/518 |

FOREIGN PATENT DOCUMENTS

| | | |
|---|---|---|
| JP | 60-153023 | 8/1985 |
| JP | H07-0167798 | 7/1995 |
| JP | 07-286953 | 10/1995 |
| JP | 11-108838 | 4/1999 |
| JP | 2001-108684 A | 4/2001 |
| JP | 2001-249013 A | 9/2001 |
| JP | 2001-272515 A | 10/2001 |
| JP | 2002-526790 A | 8/2002 |
| JP | 05-297318 B2 | 9/2013 |
| WO | 00/06996 A1 | 2/2000 |
| WO | 00/19264 A1 | 4/2000 |
| WO | 01/02846 A1 | 1/2001 |

OTHER PUBLICATIONS

European Office Action for Application No. 04786510.0, dated Dec. 28, 2007.
Examination Report issued in Australian Application No. 2004264628, dated Apr. 24, 2009.
Examination Report issued in Indian Application No. 870/CHENP/2006, with reference date of Sep. 6, 2010.
International Preliminary Report on Patentability issued in International Application No. PCT/US2004/026467, dated Nov. 1, 2006.
International Search Report issued in International Application No. PCT/US2004/026467, mailed Oct. 2, 2006.
Office Action issued in Japanese Application No. 2006-523430, dated Jun. 2, 2009.
Office Action issued in Chinese Application No. 200480030084.8, dated Jan. 22, 2010.
Office Action issued in Chinese Application No. 200480030084.8, dated May 8, 2009.
Office Action issued in Canadian Application No. 2,535,390, dated Mar. 16, 2011.
Office Action issued in Chinese Application No. 200480030084.8, dated Feb. 1, 2012.
Office Action issued in Chinese Application No. 200480030084.8, dated Jul. 1, 2011.
Office Action issued in Japanese Application No. 2006-523430, dated Feb. 23, 2010.
Office Action issued in Japanese Application No. 2009-202457, dated Nov. 15, 2011.
Office Action issued in Korean Application No. 10-2006-7002936, dated Nov. 30, 2011.
Official Notification issued in Israeli Application No. 173613, dated Dec. 15, 2009.
Rejection Decision issued in Chinese Application No. 200480030084.8, dated Aug. 2, 2010.
Supplementary European Search Report issued in European Application No. 04786510.0-1524, mailed Dec. 28, 2007.
Supplementary Partial European Search Report issued in European Application No. 04786510.0-1524, mailed Sep. 6, 2007.
Written Opinion issued in International Application No. PCT/US2004/026467, mailed Oct. 2, 2006.

* cited by examiner

| Spot Width | Groove Spacing | Groove Inclination, G | Incident Angle, I |
|---|---|---|---|
| 30 | 540 | 22.6 | 32.2 |
| 50 | 550 | 24.7 | 30.1 |
| 70 | 560 | 27.2 | 27.9 |
| 100 | 575 | 29.7 | 25 |

OPTICAL DETECTOR FOR A PARTICLE SORTING SYSTEM

RELATED APPLICATIONS

The present application is a Continuation of U.S. patent application Ser. No. 12/966,654 filed Dec. 13, 2010, entitled "Optical Detector for a Particle Sorting System", which, in turn, is a Continuation of U.S. patent application Ser. No. 12/370,237 filed Feb. 12, 2009, entitled "Optical Detector for a Particle Sorting System", which, in turn, is a Continuation of U.S. patent application Ser. No. 11/906,621 filed Oct. 3, 2007, entitled "Optical Detector for a Particle Sorting System", which, in turn, is a Divisional of U.S. patent application Ser. No. 10/915,016 filed Aug. 9, 2004, entitled "Optical Detector for a Particle Sorting System", which, in turn, claims priority to U.S. Provisional Patent Application Ser. No. 60/495,374, filed Aug. 14, 2003, the contents of each identified application are hereby expressly incorporated by reference in their entirety. This application is also related to U.S. patent application Ser. No. 11/506,522 filed Aug. 18, 2006 as well as U.S. patent application Ser. No. 12/079,457 filed Mar. 27, 2008, the contents of each identified application are hereby expressly incorporated by reference in their entirety.

FIELD OF THE INVENTION

The present invention relates to a system and method for monitoring particles flowing through a channel.

BACKGROUND OF THE INVENTION

In a system, such as a microfluidic system, that conveys particles through one or more channels, an optical system may be used for monitoring, analyzing or detecting the particles. Optical systems may be useful, for example in particle sorting systems, which sort a stream of particles flowing through one or more channels based on a predetermined characteristic.

Conventional detection systems have significant drawbacks. For example, prior optical detection systems are at times inaccurate and provide poor results due to the difficulty of observing low light level signals from fluorescent labels on particles when spread out over a large area. Prior optical systems also have difficulty when the light signals to be detected are of short duration, for example, less than one millisecond. For example, conventional CCD (charge coupled device) technology has a frame rate of more than one millisecond.

Prior systems for interrogating microchannels also are limited to focusing light on a single channel, a region of less than about 500 um, and capturing light from a similarly limited region.

SUMMARY OF THE INVENTION

The present invention provides an optical system for acquiring fast spectra from spatially channel arrays. The system is designed to be used to interrogate a microfluidic particle analysis or sorting chip that contains an array of one or more parallel fluidic channels spaced over 1 to 200 millimeters. The particles conveyed in the channels have velocities from 0.1 to 10 meters per second, therefore the signals observed by the detectors may be sub-millisecond in duration and may require observation with 1 to 100 Megahertz bandwidth detectors and electronics.

The optical detection system includes a light source for producing a light beam that passes through the microfluidic chip or the channel to be monitored, one or more lenses or optical fibers for capturing the light from the light source after interaction with the particles or chemicals in the microfluidic channels, and one or more detectors. The detectors, which may include light amplifying elements, detect each light signal and transduce the light signal into an electronic signal. The electronic signals, each representing the intensity of an optical signal, pass from each detector to an electronic data acquisition system for analysis. The light amplifying element or elements may comprise an array of phototubes, a multianode phototube, or a multichannel plate based image intensifier coupled to an array of photodiode detectors.

The optical system cost effectively and simultaneously captures extinction signals, one or more optical scatter signals, and one or more fluorescence signals all at low light levels and at high bandwidth (>1 MHz) from an array of one or more particle conveying channels at once. The system provides efficient and accurate monitoring of each particle under various conditions.

BRIEF DESCRIPTION OF THE FIGURES

The invention will be apparent from the description herein and the accompanying drawings, in which like reference characters refer to the same parts throughout the different views.

DETAILED DESCRIPTION OF THE INVENTION

The present invention provides an optical system for monitoring and detecting particle flow through an array of channels. The present invention will be described below relative to illustrative embodiments. Those skilled in the art will appreciate that the present invention may be implemented in a number of different applications and embodiments and is not specifically limited in its application to the particular embodiments depicted herein.

Figure 1:
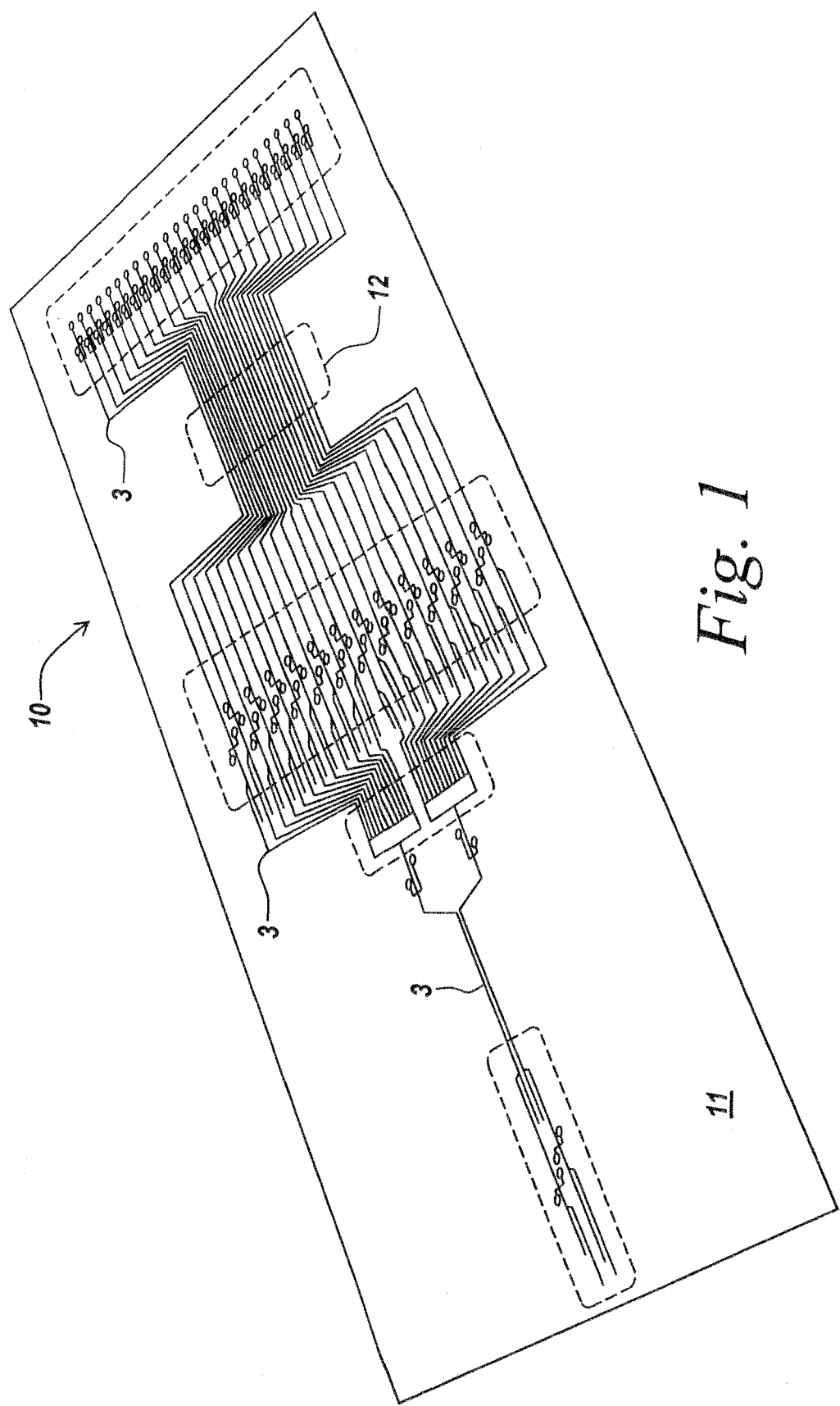
FIG. 1 illustrates a system having a plurality of channels for conveying streams of particles, suitable for implementing an illustrative embodiment of the present invention.

FIG. 1 illustrates a microfluidic system 10 suitable for implementing an illustrative embodiment of the invention, including a plurality of channels for conveying a substance, such as particles or cells, therethrough. The illustrative microfluidic system 10 comprises a substrate 1 having a plurality of channels, such as microchannels 3, disposed therein. The channels transport fluid and/or particles through the microfluidic system 10 for processing, handling, and/or performing any suitable operation on a liquid sample. As used herein, the term "microfluidic" refers to a system or device for handling, processing, ejecting and/or analyzing a fluid sample including at least one channel having microscale dimensions. The term "channel" as used herein refers to a pathway formed in or through a medium that allows for movement of fluids, such as liquids and gases. The term "microchannel" refers to a channel preferably formed in a microfluidic system or device having cross-sectional dimensions in the range between about 1.0 µm and about 500 µm, preferably between about 25 µm and about 350 µm and most preferably between about 50 µm and about 300 µm. One of ordinary skill in the art will be able to determine an appropriate volume and length of the channel. The ranges are intended to include the above-recited values as upper or lower limits. The channel can have any selected shape or arrangement, examples of which include a linear or non-linear configuration and a U-shaped configuration. The microfluidic system 10 may comprise any suitable number of microchannels 3 for transporting fluids through the microfluidic system 10.

The present invention provides an optical detector for use with a microfluidic chip, such as the microfluidic system of FIG. 1. The optical detector of the present invention may be implemented in a measurement region 2 of the microfluidic system to interrogate the system in this region. The invention provides facilitates building of a detection system that can scale to microfluidic chips with parallel arrays of channels from 1 to 200 channels laid out over one or more interrogation regions 2, that have physical extent from 1 to 250 mm with preferred extent from 1 to 100 mm.

The optical detector may monitor flow through a plurality of channels in the chip simultaneously. The optical detector or a system of optical detectors can inspect individual particles for one or more particular characteristics, such as size, form, fluorescent intensity optical scattering, as well as other characteristics obvious to one of ordinary skill. For example, in an illustrative embodiment, the optical detector of the present invention can be positioned over a relatively large area of the chip (e.g., an active area of between about twelve millimeters and fifty millimeters in diameter) containing over one-hundred channels of flowing particles to be observed. The optical detector is capable of cost effectively capturing fast, low light level, signals from a plurality or all of the channels at once. One skilled in the art will recognize that the optical system is not limited to use in particle or cell sorting systems and may be implemented in any suitable system having a substance, such as particles, to be monitored flowing through one or more channels.

Figure 2:
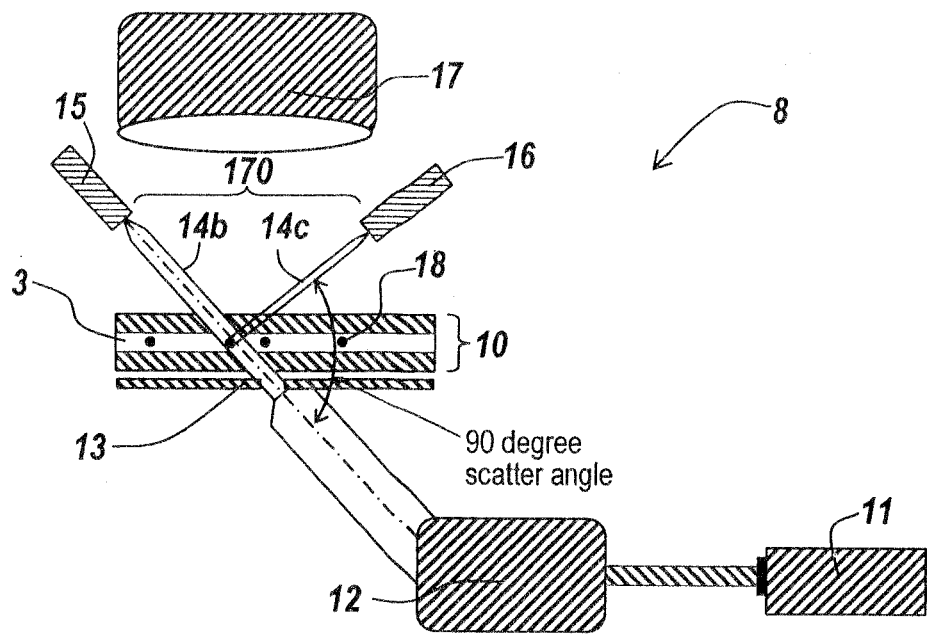
FIG. 2 is a schematic diagram of an optical detection system of the present invention.

FIG. 2 illustrates an overview of an optical detection system 8 of an illustrative embodiment of the invention, which may be implemented in the microfluidic system of FIG. 1. Those skilled in the art will recognize that the optical detection system may be implemented in any suitable system and is not limited to the microfluidic system of FIG. 1.

The optical detection system 8 includes a light source 11, illustrated as a laser, coupled to beam shaping optics 12 for producing and forming a beam of light 14 that passes through an optical mask 13, illustrated as an array of pinholes aligned with an array of particle conveying channels 3 in the microfluidic chip 10. The light admitted by the pinholes subsequently passes through the conveying channels 3 themselves. The light beam admitted to each channel via one or more associated pin holes intersects particles 18 are conveyed through the channel 3 to create optical signals. Examples of optical signals that can be produced in optical particle analysis, cytometry or sorting when a light beam intersects a particle include optical extinction, angle dependent optical scatter and fluorescent light. Optical extinction refers to the amount of light that passes the particle without interacting. Angle dependent optical scatter refers to the fraction of light that is scattered or bent at each angle (theta) away from the incident light beam. Fluorescent light is light that is absorbed by molecules in the particle and re-emitted at a longer wavelength.

Detector optics 15, 16, 17, located on an opposite side of the channel 3 from the light source 11, capture and observe the optical signals generated by the intersection of a light beam with a particle in a channel. Optical Extinction detectors 15 are placed directly opposite the light source 11 and aligned with the incident light path 14 for detecting optical extinction. Optical scatter detectors 16 are placed substantially perpendicular to the incident light path 14 in the plane formed by the incident light vector and the microfluidic channel it intersects. Preferably, the optical scatter detectors are located at an angle of about 90 degrees relative to the incident light path 14. Optical Scatter detectors for other angles may optionally be placed at those angles in that same plane. A fluorescence detection subsystem 17 captures optical signals from fluorescence. The fluorescence detection subsystem 17 may include a large high numerical aperture lens and accompanying optical elements. As shown, the fluorescence detection subsystem is placed above the microfluidic chip 10 to capture as many fluorescent photons as possible and image them onto detectors (not shown).

The optical detection system 8 may be implemented in an interrogation area 2 of the chip 10. The illustrative interrogation area 2 encompasses 24 channels 3, though one skilled in the art will recognize that any suitable number of channels may be observed using the optical detection system 8. In the illustrative embodiment, the interrogation area 2 is about 10 mm wide (across a plurality of channels 3) by 4 mm long (along each channel 3), though one skilled in the art will recognize that the invention is not limited to this range When light 14 from a laser 11 or other optical source is incident on the chip 10, only light that passes through the narrow region that particles follow can interact with particles to produce an optical signal. Light that passes through the chip 10 outside of the channels 3 or light that passes through a region of a channel that does not contain the particles can contribute only to background or noise and not to signal and therefore is stray light and should be minimized. It is also a consideration that light which passes through the chip without passing through the particles to be observed represents wasted laser source power and should therefore be minimized for cost and thermal management reasons. The optical mask 13, formed by the layer of pinholes, and the beam shaping optics 12 both minimize stray light and minimizes waste of laser power.

As shown, the light source 11 provides the incident light at about a 45-degree angle relative to the channel 3. In this manner, the forward scatter/extinction extends in the same direction on the opposite side of the channel 3. As shown, the forward scatter 14b extends at a 45-degree angle from the channel 3. The side scatter 14c extends about 90 degrees from the incident light, providing the fluorescence optics 17 a cone of mechanical freedom 170. The cone of mechanical freedom 170 provides a 90 degree unobstructed view for the detector in between the forward scatter 14b and side scatter 14c.

Figure 3:
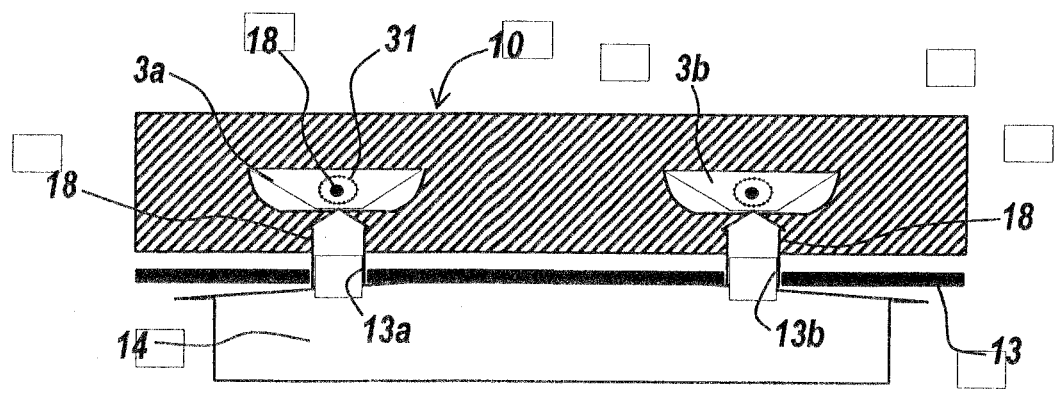
FIG. 3 illustrates a cross section through one microchannel in a plane perpendicular to the microchannel

FIG. 3 shows an illustrative picture of the cross section through a part of a microfluidic chip 10 containing a pair of microchannels 3a and 3b. The cross-section is in a plane that cuts through the microchannels and the pinholes 13a, 13b of the mask 13. The incident light 14 is partly blocked by the pinhole layer 13 and narrows the initial beam 14 to focused beams 18 defined by each pinhole 13a, 13b. The focused beams 18 intersect each channel to illuminate the region 31 in which particles 18 are permitted to flow in a conventional core flow. Much stray light is blocked by the pinhole layer 13, which may be a separate part from the microfluidic chip or may be fabricated on the surface of the chip by photolithography or other methods known to those skilled in the art of chip fabrication.

The microfluidic system may comprise any system including channels for flowing a substance, such as particles or cells, therethrough. For example, the microfluidic system 10 may comprise a particle sorting system, such as the particle sorting systems described in U.S. patent application Ser. Nos. 10/179,488 and 10/329,008, the contents of both patent applications are herein incorporated by reference. Other suitable microfluidic systems are described in U.S. patent application Ser. Nos. 10/028,852 10/027,484, 10/027,516 and 10/607,287, all of which are herein incorporated by reference.

Figure 4:
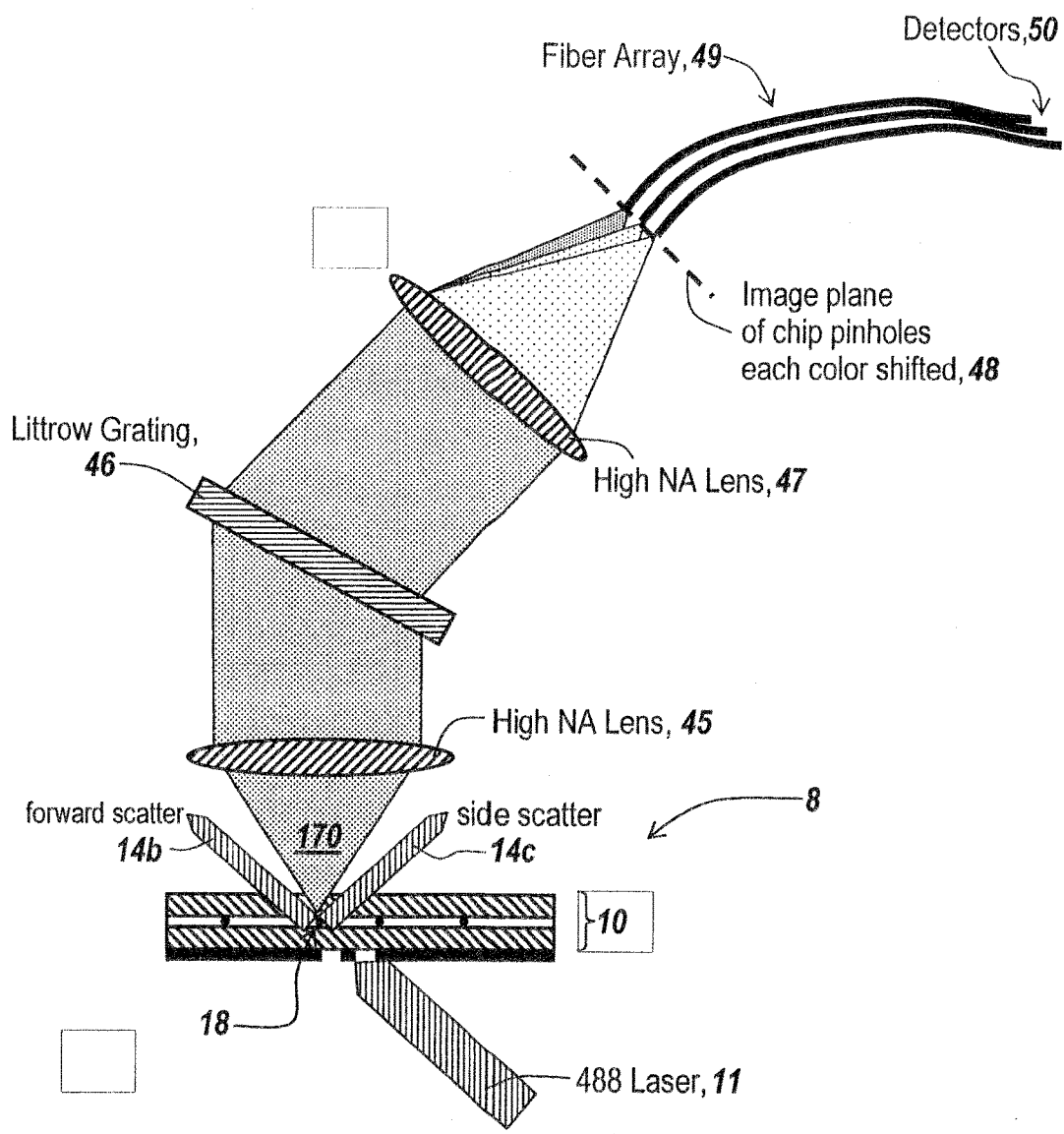
FIG. 4 is a schematic diagram of an optical detection system of the present invention, illustrating in detail the components of the fluorescence detector.

FIG. 4 illustrates a schematic diagram of the optical detection system of FIG. 2 illustrating in detail the components of the fluorescence detection subsystem 17. The fluorescence detection subsystem 17 includes a high numerical aperture (low F#) collection lens 45 configured and positioned to capture as many of the photons emitted from the illuminated particle as possible. The lens 45 may be an off the shelf F#=1 lenses of 50 mm and focal length commercially available. An example is the Leica Noctilux 50 mm F#1 lens. Larger lenses are also available and in use for imaging multiwell plates. A dispersive element 46, illustrated as a littrow grating, is located above the first collection lens 45. The dispersive element 46 bends light in a manner related to the wavelength of the particular light beam. The illustrative littrow grating 46 grating is 76.2 mm in diameter with a 73 mm active area. The littrow grating 46 has 720 grooves/mm and has a blaze angle of 43.1 degrees at 550 nm (the angle that the grating is positioned from the vertical). The Littrow angle is 23.33 degrees which is the angle that 550 nm light is bent away from the vertical in FIG. 4. One skilled in the art will recognize that any suitable means for bending light in a particular manner may be used in accordance with the teachings of the invention. A reconstruction lens 47 is positioned at the littrow angle to catch the 1$^{st}$ order diffraction light from the grating 46 and reconstruct the diffracted light into an image of the illuminated particle in the image plane 48.

A fiber array 49 extends from the image plane 48 and conveys signals to detectors 50 for analyzing the signal. The detectors may be a camera or other suitable device.

Due to the presence of the littrow grating in the optical path the illuminated particle in the microchannel 3 is imaged into the plane 48 with longer wavelength photons tilted through a larger angle than shorter wavelength photons so that the particle has a spectra spread over that image plane. Photons having wavelength from 500 nm to 700 nm are spread over about 7841 microns in the image plane 48 for the 50 mm focal length lenses used for lenses 45 and 47. The illustrative embodiment has a spectral resolution of 39.2 microns per nm wavelength.

The optical detection system 8 can be used to observe particles labeled with antibodies bound to fluorophores or other fluorescent particle markers known to those skilled in the art of cytometry. When the excitation light is of 488 nm wavelength then, for example, one can use particles labeled with antibodies bound to fluorophores FITC (fluorescein isothiocyanate), PE (R-Phycoerythrin), APC (AlloPhycoCyanin) and PerCP (Peridinin-chlorophyll-protein Complex) which have peak fluorescence emission at 530 nm, 575 nm, 630 nm, and 695 nm respectively. The photons from FITC, PE, and PerCP are placed onto the image plane at positions −784 microns, 980 microns, 3136 nm, and 5684 microns, (relative to 0 at 550 nm) respectively. An opaque plate with 400 um holes in it and 400 um diameter optical fibers placed in those holes will then give each fiber 49 a wavelength capture bandwidth of about 10 nm. Placing a fiber 49 at each location corresponding to the peak emission of desirable fluorophores produces an efficient and compact multiple color detection system. Fibers 49 placed with one end in the image plane 48 have their other end attached to a detector. In the illustrative embodiment, the second end of the fibers is coupled to the photocathode window of a phototube (for example single anode H6780-20 or 32-anode H7260-20 phototubes from Hamamatsu Inc.) at a location corresponding to a single anode, in order to amplify the fluorescence optical signals and convert them to electronic signals. Other amplifying light detectors such as image intensifiers or avalanche photodiode arrays or others known to those skilled in the art of optics may also be used to detect the optical signals and convert them into electronic signals.

In FIG. 4, the fibers 49 which interrogate particles in the illustrated channel are located in the same plane as the plane of the channel in the microfluidic chip. If the system is used on a multiple channel array then the other channels lie in front of the plane of illustrated channel or behind the plane of illustrated channel.

Figure 5:
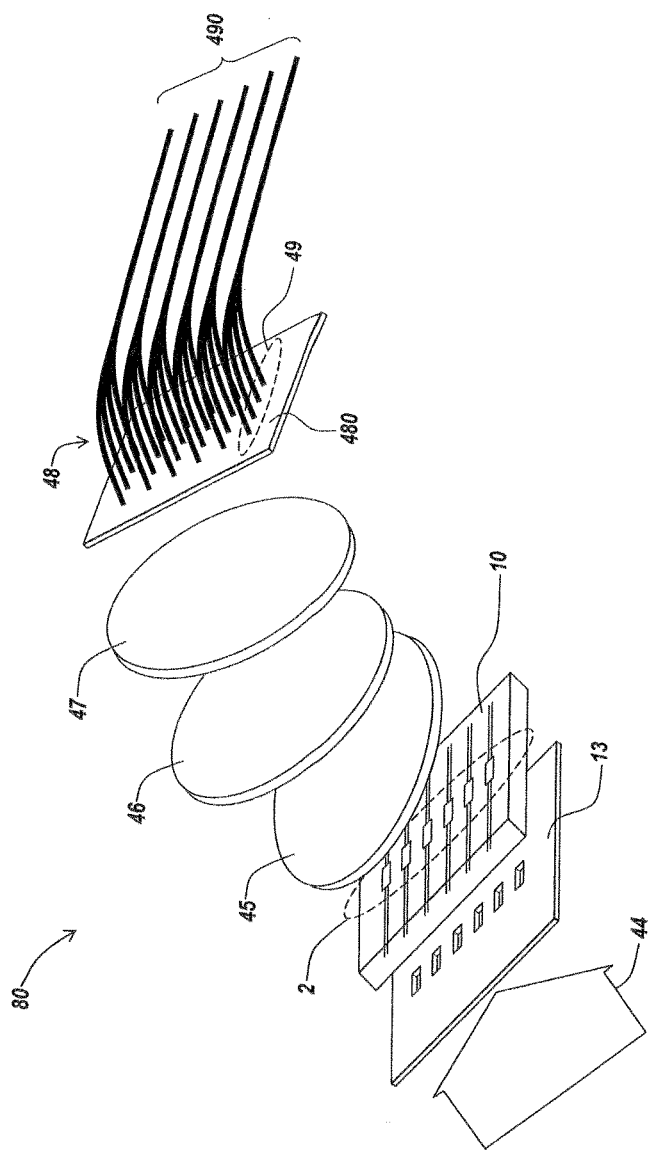
FIG. 5 illustrates an optical detection system suitable for analyzing particles in a plurality of channels of a microfluidic system.

FIG. 5 shows a perspective view of an optical detector system 80 used for observing multiple channels in a microfluidic chip. The optical detector system 80 also includes a pinhole array 13 blocking most incident light 14 and illuminating small detection regions 2 in each channel 3 of the six channels of the microfluidic chip. The optical column of the collection lens, littrow grating and reconstruction lens is similar to that shown in FIG. 4, and can have the same embodiments of lens and grating specifications. In general, the size of the components of lens and grating sets must be sufficient to give a field of view on the chip in excess of the size of the detection region (the region where channels are illuminated through pinholes). In the image plane 48 there is placed a plate 480 holding six arrays 490, including four fibers each. Each array of four optical fibers 49 is positioned to sample the optical spectra emitted from an associated channel 3. Each fiber in the array is positioned on the peak emission location of one fluorophore. High numerical aperture fibers or lensed fibers are appropriate here as will be apparent to those skilled in the art.

Figure 6A:
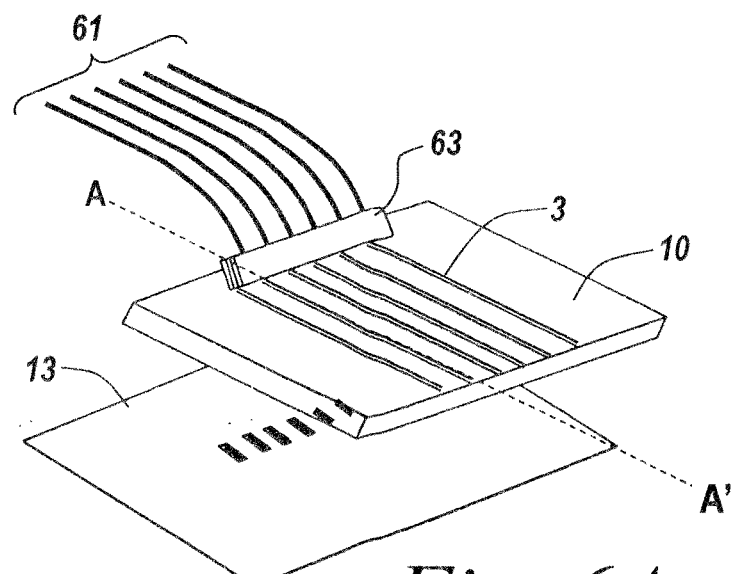
FIGS. 6A-6C shows an embodiment of the subsystem for detecting optical scatter at a 90 degree angle or extinction in the optical detection system of FIG. 2.
Figure 6B:
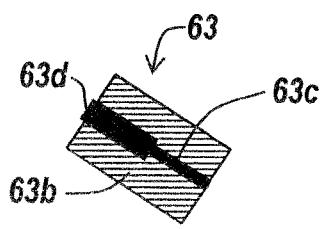
Figure 6C:
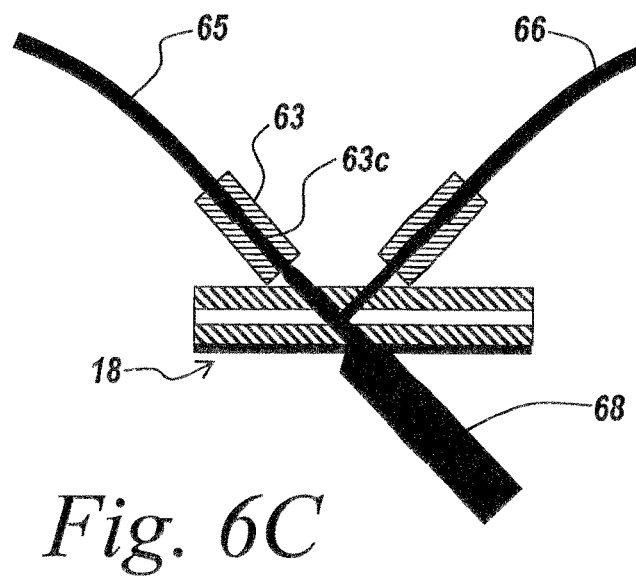

FIGS. 6A-6C shows an embodiment of the subsystem for detecting optical scatter at a 90 degree angle or extinction. In this embodiment, an optical extenciton columnated detector ribbon 63 is positioned above a multichannel chip 10 with interchannel spacing of about 500 microns. The optical extenciton columnated detector ribbon 63, a cross-section of which is shown in FIG. 6B, is a mechanical part with 300 micron diameter holes drilled in it to a depth of less than the ribbon thickness 63d, and spaced 500 microns on centers so as to line up the holes with channel spacing. A high numerical aperture fiber 65 is placed into each hole to form an array of fibers 61, with one fiber per channel. A columnating hole of smaller diameter but concentric with the fiber hole 63c is drilled in each hole. This columnating hole penetrates the ribbon connector 63b, and allows light to pass through the columnating hole 63c and into the fiber 65 positioned in the larger diameter shaft. To make this subsystem work, the incident light 68 intersects the pinhole and channel at a near 45 degree angle and the optical extinction detection ribbon 63 is mounted directly along the incident light vector (i.e. at an angle of 180 degrees to the incident light) as shown by the position of the ribbon. The aperture of the columnator must be in excess of the aperture of the pinhole so that for well columnated incident light all of the light that crosses the pinhole may be detected in the fiber at the end of the columnator. The columnator itself is chosen to be long enough to reject any stray light from other channels. For example, in one embodiment, the pinhole aperture is 150 micron diameter, the columnator is 250 micron diameter, the fiber is 300 micron diameter, and the collimator, which is positioned within 2 mm of the channel, is 1 mm long. At the far end of the fiber array 61, each fiber is attached to a phototube or other optical detector. Optical extinction is often sufficiently bright to use a photodiode for its detector.

In FIG. 6C, a second ribbon 66 constructed substantially the same as the first described ribbon 63 but positioned at 90 degrees from the incident light which is appropriate for measuring 90 degree scatter or side scatter signals from cells or particles. One skilled in the art will recognize that similar ribbons may be positioned at other angles to observe other scattering parameters. A particular angle of interest is so called forward scatter which is optical scattering in the almost forward direction generally as close to direct forward positioning (nearly 180 degrees from incident) without acquiring straight through light in the extinction path.

In a further embodiment, the light source 11 is a Coherent Sapphire 488/200 laser, which is a small, air-cooled solid state device producing about 200 mw with little or no noise from gas laser tube emissions. Alternatively, an OPSS (optically pumped solid state) laser is used, which is also capable of generating all the different excitation wavelengths needed to perform monitoring. One skilled in the art will recognize that any suitable light source may be used.

Figure 7:
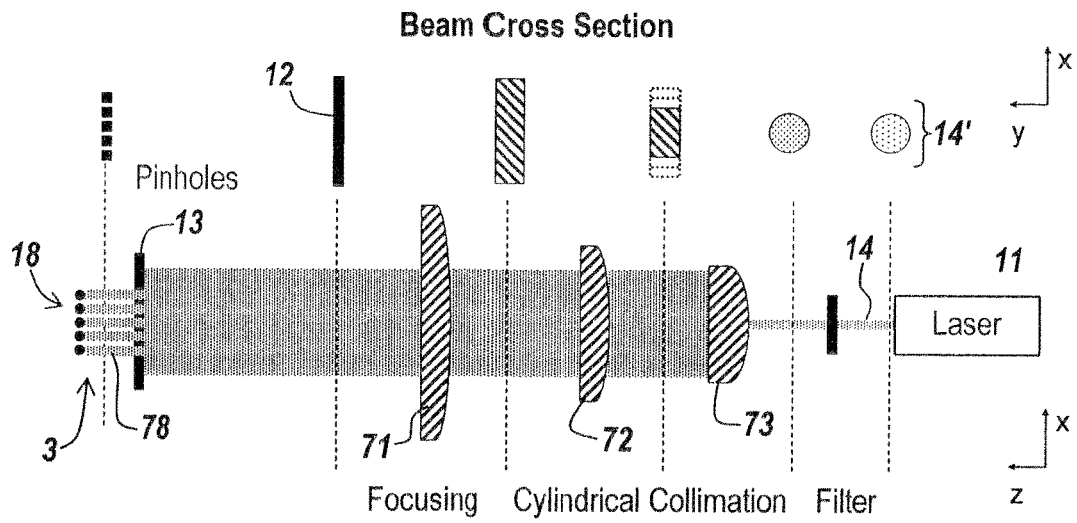
FIG. 7 is a schematic of beam shaping optics suitable for use in the optical detection system of FIG. 2.

FIG. 7 is a cross-section of one embodiment of beam shaping optics 12 suitable for use with the optical detector of the illustrative embodiment of the invention. The optical schematic is drawn in the x-z plane with the overall direction of light propagation along the z axis. Each dotted line leads up to a light beam x-y profile sketch 14' to show how the beam is manipulated by the shaping optics. The beam passes from a single laser 11 output of nearly round profile 700 microns in diameter to a wavelength filtered beam after a low pass or band pass filter 74. The beam then passes through a first pair of cylindrical collimation lenses 73 having focal length 5 mm having focal length 250 mm, which produces a substantially rectangular-shaped beam. The beam then passes through a focusing lens 71 having focal length is a 150 mm cylindrical lens to sharpen the beam 14 to 100 microns in the y-axis. The overall profile in this embodiment after the focusing lens 71 is 36 mm by 100 micron and can be used to illuminate a pinhole array 13 of up to seventy pinholes/channels at 500 micron spacing. Since the pinholes are less than about 100 microns in the direction of the y-axis, the limitation of the beam prevents waste of the light. In an N pinhole chip spaced 500 microns on centers it is preferable for the beam to be slightly more than 500×N microns along the x-axis and 200 microns along the y-axis (slightly more than 100 microns) in order to minimize wasted laser power. The columnated and shaped beam then intersects the pinhole array 13 and becomes N pinhole shaped beams 78 that are spaced to intersect the matching array of channels 3.

The beam shaping embodiment of FIG. 7 is very usable allowing minimal stray light and acceptable power efficiency of about 10% considering that this design allows simultaneous observation of fast (bandwidth>10 MHZ) extinction, scatter, and fluorescence from many channels at once.

Figures 8, 10:
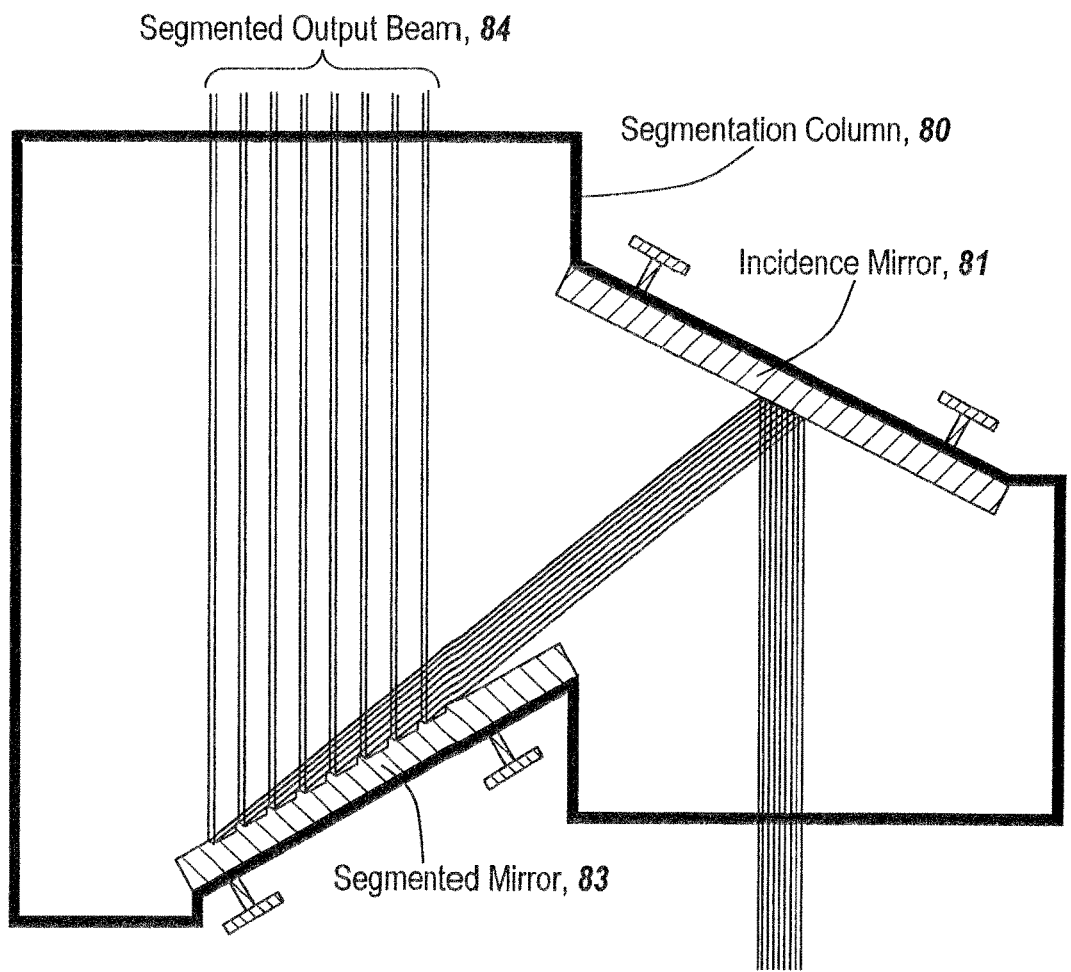
FIG. 8 illustrates a segmented mirror suitable for using in the optical detection system of the present invention.
FIG. 10 is a table showing different configurations for a groove of the segmented mirror based on a corresponding spot width.

FIG. 8 shows a reflective beam splitter 80 based on a grooved mirror, suitable for use in the optical detection system of the present invention. The beam splitter 80 includes a segmented mirror 83 for splitting an incoming light beam into a plurality of beams. A columnated incident beam 82 enters the splitter 80 and is reflected off an incidence mirror 81 which is used to set the correct angle of incidence (generally a low angle) for the beam on the segmented mirror 83, which splits the incident beam into an array of smaller beams 84. The array of smaller beams 84 extend upwards parallel to the incident beam 82.

The segmented mirror 83 comprises a uniform array of reflective grooves. Preferably, the uniform array comprises anisotropically etched silicon. Alternatively, the uniform array of grooves is made out of conventionally machined metal with an optical finish. In another embodiment, the uniform array of grooves formed in a plastic material, which is then covered with a reflective coating to for the array of grooves.

Figure 9:
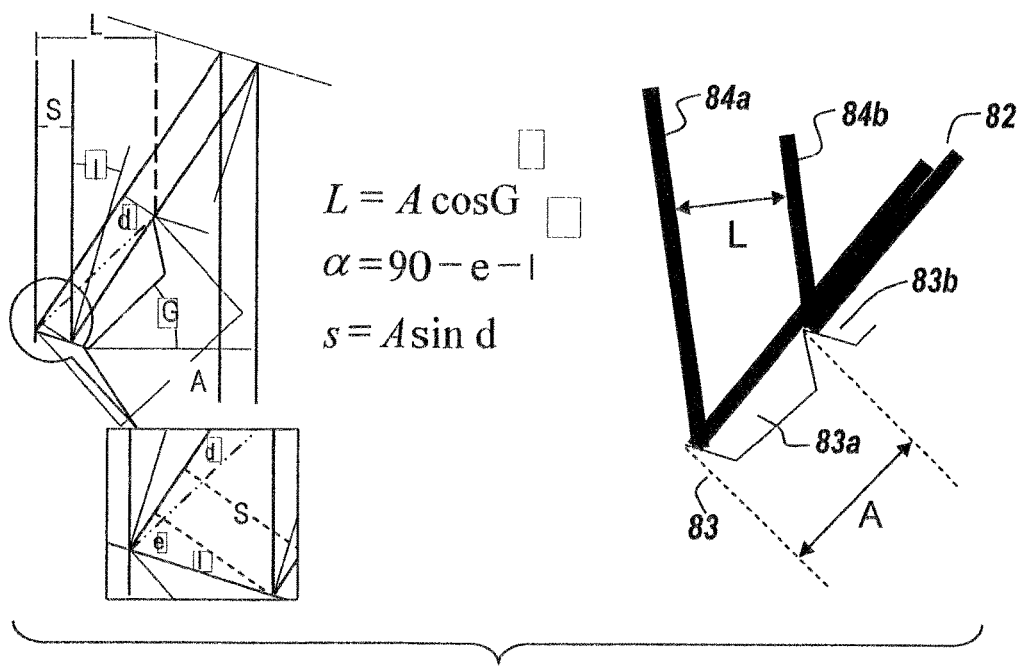
FIG. 9 is a partial view of a groove of the segmented mirror of FIG. 8.

FIG. 9 shows the angles and formulas guiding the design of such segmented mirrors. The incident beam 82 is partly clipped by each groove 83a in the mirror and that clipped part is reflected off at a fixed angle to make a narrower beam 84a. A second narrow beam 84b is formed by an adjacent groove 84b. Each groove is separated by the groove spacing A and the splitter generates beams of uniform spot width (assuming uniform grooves) and beam or lane spacing L which we design to match the pinhole and channel spacing in the microfluidic chip.

FIG. 10 is a table of embodiments of the beam splitter of FIG. 8 where lane spacing L is 500 microns and the grooves are fabricated with silicon anisotropic etching (which has a fixed groove angle e=54.74) The table indicates a suitable mirror configuration for a selected spot size. For example, a 100 micron spot size, is suitable for pinholes <100 microns, corresponds to a groove spacing A=575 microns, groove inclination G=29.7 degrees and incident angle I=25 degrees.

Figure 11:
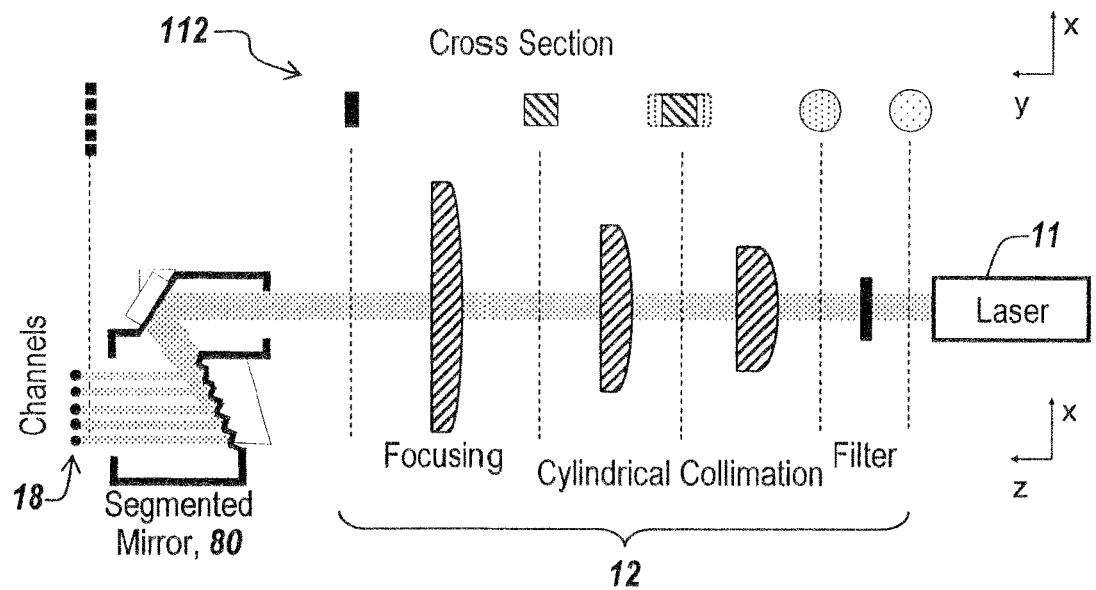
FIG. 11 is a schematic of beam shaping optics employing a segmented mirror in an optical detection system of an illustrative embodiment of the invention.

FIG. 11 sketches an embodiment of the beam shaping subsystem 112 suitable for use in the optical detector system. The illustrative beam shaping subsystem 112 makes use of a segmented mirror 80, such as the segmented mirror of FIG. 8, in a final stage after employing similar beam shaping optics 12 similar to the beam shaping optics 12 described with respect to FIG. 7.

An alternative embodiment includes fabricating the pinhole arrays 13 on each microfluidic chip rather than having them separately mounted on the optical system.

An alternative embodiment to the detectors for the array of fibers used in the image plane of FIGS. 4 and 5 is to place an image intensifier in that plane and place fibers behind that image intensifier to readout the optical signal it produces on its phosphor. Such an alternative may reduce costs by using only one light amplifying element (the image intensifier) for all the fluorescence signals, and then photodiodes for conversion of post-image intensifier optical signals to electronic signals.

Figure 12:
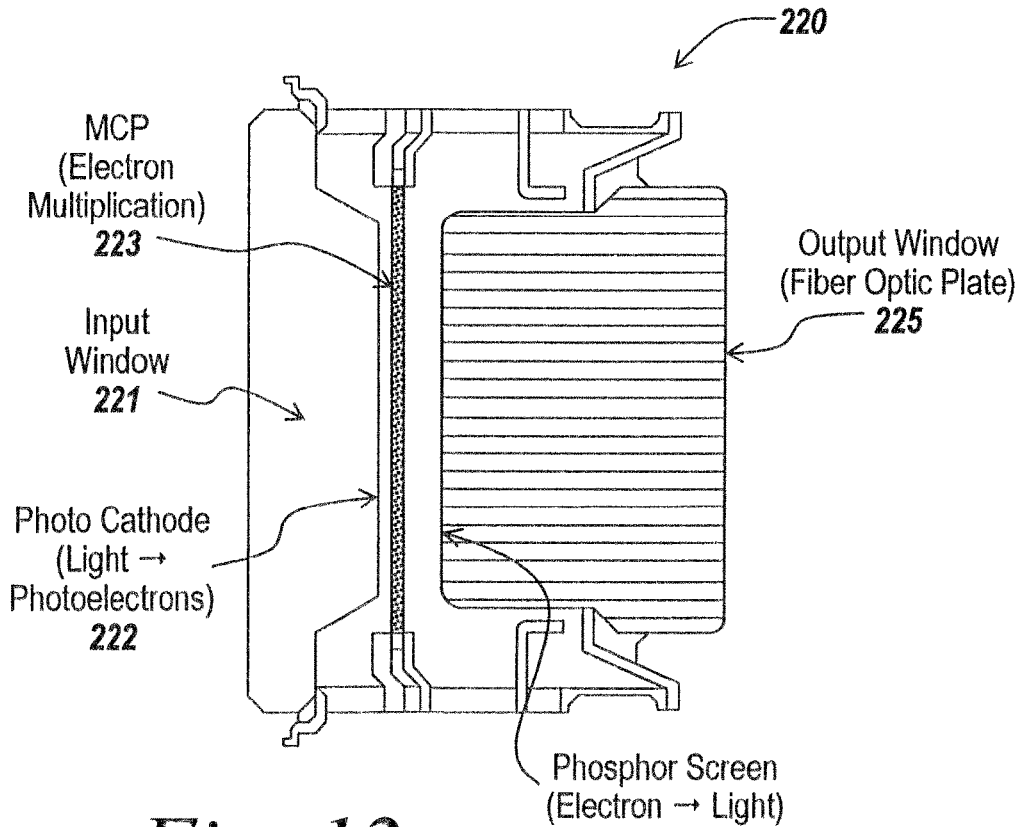
FIG. 12 illustrates an image intensifier suitable for use with the optical detection system of an illustrative embodiment of the invention.

FIG. 12 shows a picture of a standard Hamamatsu image intensifier 220 but one skilled in the art will recognize that any large area light amplifying component with high spatial resolution may be used in this alternative. The image intensifier 220 is used to amplify the intensity of an optical image before passing the signal to a photodiode array or other suitable detection device. As shown, the image intensifier includes an input window 221 for the image signal, a light-sensitive electron emitter, such as a photocathode 222, for transforming the light to photoelectrons, a MCP 223 for electron multiplication, a phosphor screen 224 for converting the electrons to light and an output window 225, illustrated as a fiber optic plate. According to an illustrative embodiment, the image intensifier may comprise a 25 mm-40 mm Hamamatsu image intensifier, though one skilled in the art will recognize that any suitable device may be used.

An alternative embodiment to both the beam shaping subsystem 12 and the fluorescence detection subsystem 17 includes short pass or long pass or wavelength band pass or band blocking filters to remove stray or spurious source light in the case of the fluorescence detection system or to remove stray or spurious wavelength components from the light emitted by the light source 11.

An alternative embodiment to the extinction and scatter detectors 15 and 16 is to add an independent laser power monitor to the system to use in normalizing those signals. This is useful since both of those signals are directly proportional to laser power so noise on the laser may distort those signals.

An alternative embodiment to the arrays of fibers used with the detectors 15, 16 and 17 is to replace each array of fibers with an array of photodiodes or avalanche photodiodes or other optical detector array. One skilled in the art will recognize that alternative detectors are possible here as long as they match the light level requirement of the samples and the form factor requirements of the specific chip embodiments to be used.

An alternative embodiment to the beam splitter might use reflective groove arrays manufactured by anisotropically etching crystalline materials or conventional machining of metal or forming of plastic followed by appropriate optical polishing or reflective coating In all embodiments of this invention the pinhole array is generally matched in spacing to the microfluidic channels. When a reflective beam splitter is used in the beam shaping optics it also must be matched to the pinholes.

While the simplest implementations use uniformly arrayed channels and uniformly to arrayed pinholes and possibly uniformly arrayed grooves in beam splitting this is not required by the invention and similar embodiments can be designed to use irregular spacing or patterns of channels An alternative embodiment to the fluorescence detection subsystem A7 is to add narrow bandpass filters before or after the fibers in the image plane (3-5), (2-8). a 400 micron fiber in that plane will capture a 10 nm bandwidth. Adding 10 nm or 5 nm bandpass filters will improve the sensitivity and reduce noise in some cases.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A particle processing system comprising:
   one or more electromagnetic radiation sources configured to illuminate a first particle flowing in a detection region of a first stream;
   an optical transmission path configured to receive an optical signal from the detection region, and to transmit a first color signal and a second color signal corresponding to one or more particle characteristics of the first particle; and
   a single detector operatively associated with the optical transmission path and configured to receive the first and second color signals.

2. The particle processing system of claim 1, wherein the optical transmission path includes a spectral separation element that converts the optical signal into at least the first color signal and the second color signal.

3. The particle processing system of claim 1, wherein the optical transmission path includes a first optical fiber receiving and transmitting the first color signal to the detector and a second optical fiber receiving and transmitting the second color signal to the detector.

4. The particle processing system of claim 1, wherein the optical transmission path includes an element having optically opaque regions and optically transmissive regions, the optically transmissive regions corresponding to the first and second color signals.

5. The particle processing system of claim 1, wherein the spectral bandwidth of the first color signal is approximately 10 nm.

6. The particle processing system of claim 1,
   wherein the optical transmission path includes a spectral dispersive element configured to receive the optical signal from the detection region and to provide a first spectrally-spread signal; and
   further including a first plurality of optical fibers operatively associated with the spectral dispersive element, each optical fiber of the first plurality of optical fibers positioned to receive and transmit a specific spectral bandwidth signal of the spectrally-spread signal provided by the spectral dispersive element as a color signal.

7. The particle processing system of claim 6,
   wherein the one or more electromagnetic radiation sources is configured to illuminate a second particle flowing in a second stream;
   wherein the spectral dispersive element is configured to receive a second optical signal from the second stream and to provide a second spectrally-spread signal; and
   further comprising a second plurality of optical fibers associated with the spectral dispersive element, each optical fiber associated with the second plurality of optical fibers positioned to receive and transmit a specific spectral bandwidth signal of the second spectrally-spread signal provided by the spectral dispersive element; and wherein the detector is operatively associated with the first and second plurality of optical fibers for receiving the first and second plurality of specific spectral bandwidth signals.

8. The particle processing system of claim 6, further including a high numerical aperture lens located between the first stream and the first plurality of optical fibers.

9. The particle processing system of claim 1, further including a mask located between the electromagnetic radiation source and the first stream.

10. The particle processing system of claim 1, wherein the detector is a fluorescence detector.

11. The particle processing system of claim 1, further including a microfluidic chip having a plurality of microchannels, wherein the at least one electromagnetic radiation source illuminates particles within a detection region of each of the plurality of microchannels and wherein the detector is configured to receive at least first and second color signals associated with each of the plurality of microchannels.

12. A multi-color optical detection system for a microfluidic system, the optical detection system comprising:
 a spectral separation system configured to receive at least one optical signal corresponding to an interrogation of a single particle illuminated with at least one interrogation beam that is generated by at least one source of electromagnetic radiation, the spectral separation system further configured to provide a plurality of spectrally-distributed signals associated with the single particle; and
 a single detector configured to receive the plurality of spectrally-distributed signals.

13. The optical detection system of claim 12, wherein the spectral separation system includes a plurality of optical fibers configured to transmit the plurality of spectrally-distributed signals to the detector.

14. The optical detection system of claim 12, wherein the spectral separation system includes a plurality of high numerical aperture optical fibers configured to transmit the plurality of spectrally-distributed signals to the detector.

15. The optical detection system of claim 12, wherein the spectral separation system includes a spectral dispersive element.

16. The optical detection system of claim 12, wherein the spectral separation system includes a masking element.

17. A method for detecting a characteristic of a particle flowing through a particle processing system, the method comprising:
 illuminating a first particle flowing in a first stream with at least one beam generated by at least one electromagnetic radiation source;
 generating at least one optical signal corresponding to a characteristic of the first particle;
 splitting said at least one optical signal into a plurality of spectrally-distinct signals; and
 transmitting the plurality of spectrally-distinct signals to a single detector.

18. The method of claim 17, wherein the at least one optical signal corresponding to the characteristic of the first particle is a fluorescent signal.

19. The method of claim 17, wherein the step of splitting further includes splitting the at least one optical signal into a plurality of spatially-limited signals; and wherein the step of transmitting further includes transmitting the plurality of spectrally-distinct and spatially-limited signals to a single detector.

* * * * *